United States Patent [19]

Sezginer

[11] Patent Number: 5,596,274
[45] Date of Patent: Jan. 21, 1997

[54] DETERMINING BOUND AND UNBOUND FLUID VOLUMES USING NUCLEAR MAGNETIC RESONANCE PULSE SEQUENCES

[75] Inventor: Abdurrahman Sezginer, Brookfield, Conn.

[73] Assignee: Schlumberger Technology Corporation, Ridgefield, Conn.

[21] Appl. No.: 332,297

[22] Filed: Oct. 31, 1994

Related U.S. Application Data

[63] Continuation-in-part of Ser. No. 999,248, Dec. 31, 1992, Pat. No. 5,363,041.
[51] Int. Cl.$^6$ ........................................... G01R 33/
[52] U.S. Cl. ............................................ 324/303
[58] Field of Search ................... 324/303, 300, 324/307, 309

[56] References Cited

U.S. PATENT DOCUMENTS

| | | | |
|---|---|---|---|
| 4,656,422 | 5/1987 | Vail, III et al. | 324/303 |
| 4,728,892 | 3/1988 | Vinegar et al. | 324/303 |
| 4,933,638 | 6/1990 | Kenyon et al. | 324/303 |
| 4,973,111 | 11/1990 | Haacke et al. | 324/303 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,218,299 | 6/1993 | Dunkel | 324/303 |
| 5,291,137 | 3/1994 | Freedman | 324/303 |
| 5,309,098 | 5/1994 | Coates et al. | 324/303 |
| 5,363,041 | 11/1994 | Sezginer | 324/303 |
| 5,387,865 | 2/1995 | Jerosch-Herold et al. | 324/303 |
| 5,389,877 | 2/1995 | Sezginer et al. | 324/303 |

OTHER PUBLICATIONS

T. C. Farrar and E. D. Becker, "Pulse and Fourier Transform NMR", *Academic Press*, 1971, pp. 18–22.

J. P. Butler et al., "Estimating solutions of first kind integral equations with nonnegative constraints and optimal smoothing", *SIAM J. Numer. Anal.*, vol. 18, No. 3, Jun. 1981, pp. 381–397.

L. L. Latour et al., "Nuclear Magnetic Resonance Properties of Rocks at elevated Temperatures", *Journal of Coll. and Interf. Science*, vol. 150, No. 2, May 1992, pp. 535–548.

J. E. Dennis, Jr. and R. B. Schnabel, "Numerical Methods for Unconstrained Optimization and Nonlinar Equations", *Prentice Hall*, 1983, pp. 111–152.

M. Abramowitz and I. A. Stegun, Ed., "Handbook of Mathematical Functions", *Dover Publications*, 1972, pp. 228–229.

G. H. Golub and C. F. VanLoan, "Matrix Computations", *John Hopkins University Press*, 1983, pp. 208–218.

E. Anderson et al., "Lapack Users' Guide", *Society for Industrial and Applied Mathematics*, 1992, pp. 25–27.

Kleinberg et al, "T1/T2 Ratio and Frequency Dependence in Porous Sedimentary Rocks", *Jnl of Colloid and Interface Science* 158, 195–198 (1993).

Straley et al., "NMR in Partially Saturated Rocks: Laboratory Insights on Free Fluid Index and Comparison with Borehole Logs," *SPWLA meeting*, Midland, TX, 1991.

*Primary Examiner*—Sandra L. O'Shea
*Assistant Examiner*—Raymond Y. Mah
*Attorney, Agent, or Firm*—Brigitte L. Jeffery; Leonard W. Pojunas

[57] ABSTRACT

A borehole logging tool comprises a Nuclear Magnetic Resonance (NMR) tool and is pulsed according to a selected Carr Purcell-Meiboom Gill (CPMG) sequence. Because the recovery time between CPMG sequences is short, the sequence acts as a filter such that signals induced by rapidly relaxing nuclei of fluid bound in an earth formation are detected. In this manner, the NMR tool gives a direct indication bound fluid volume and fast logging speeds are achieved.

20 Claims, 6 Drawing Sheets

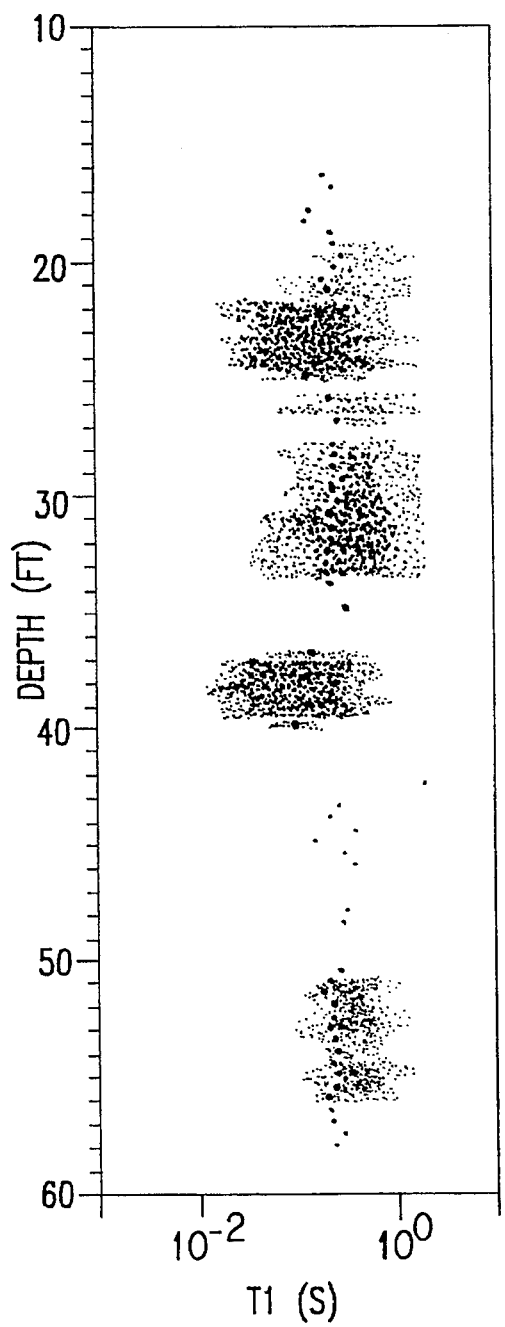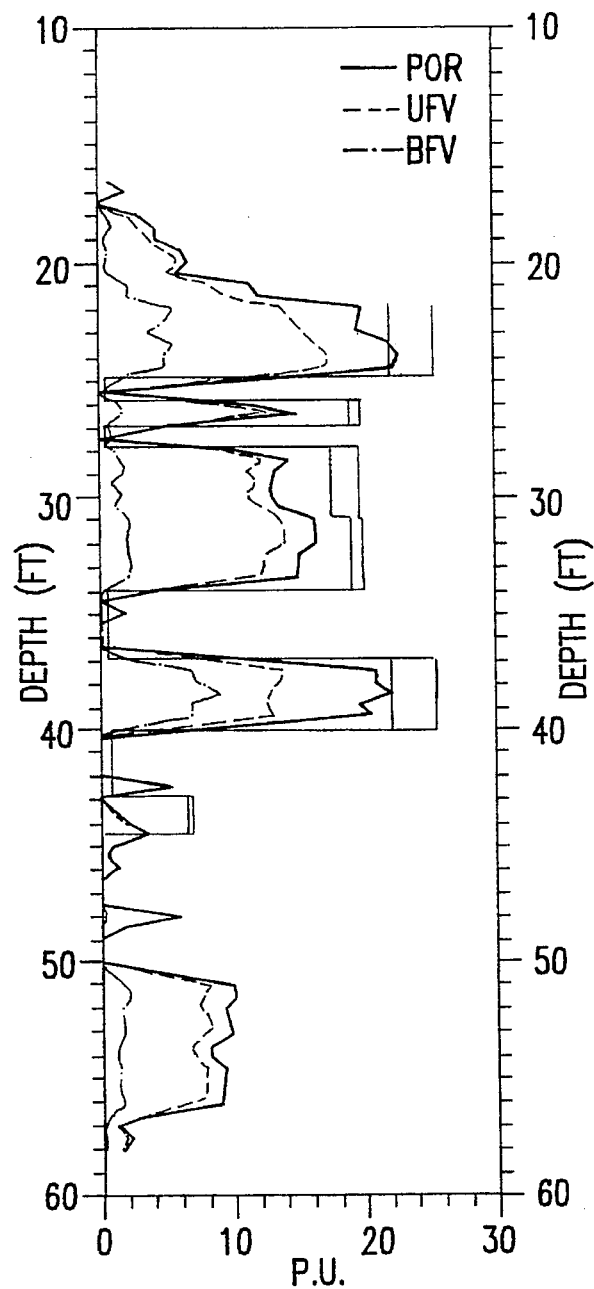
FIG.2A
FIG.2B

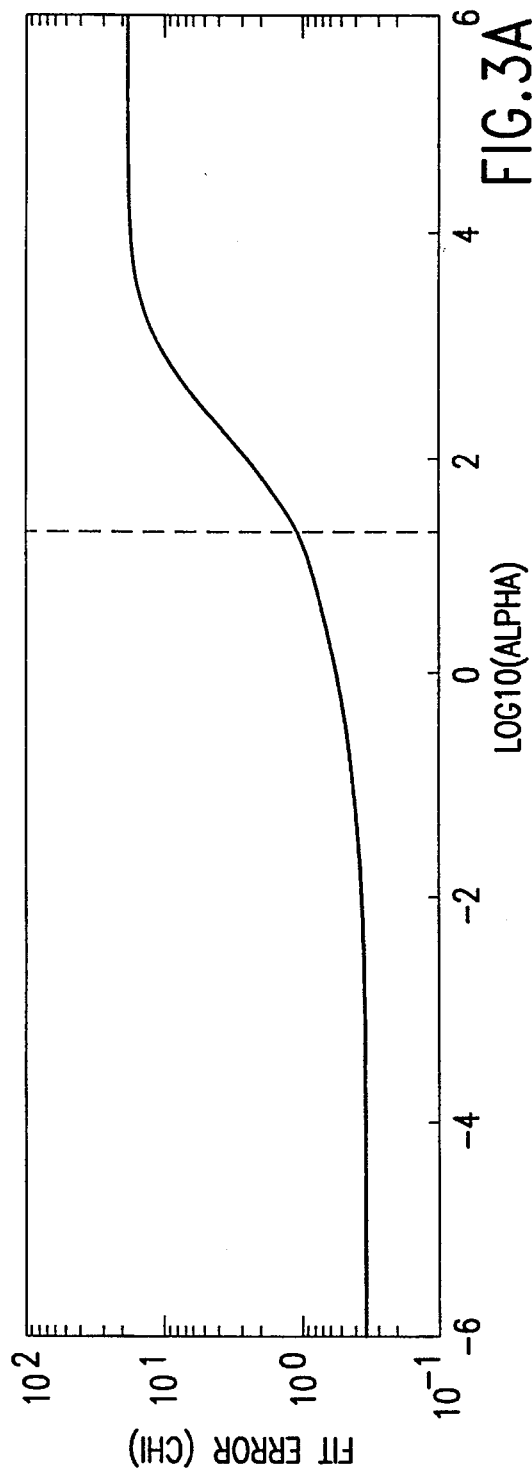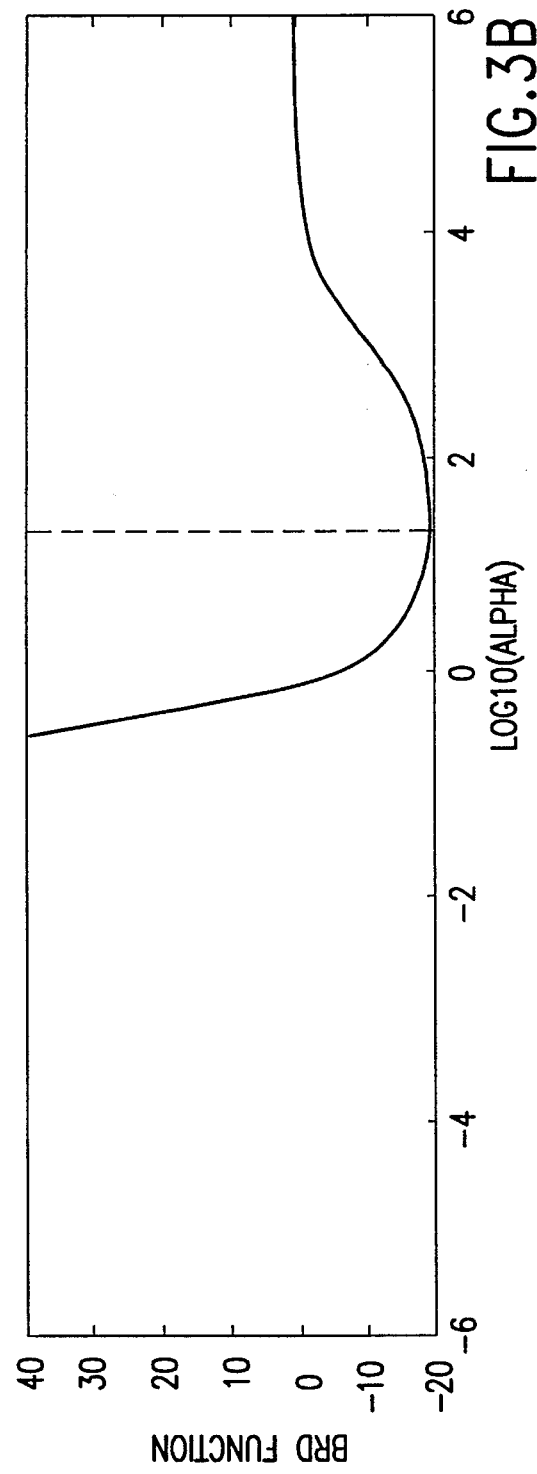

DETERMINING BOUND AND UNBOUND FLUID VOLUMES USING NUCLEAR MAGNETIC RESONANCE PULSE SEQUENCES

This is a Continuation-in-Part application of U.S. patent application Ser. No. 07/999,248, filed Dec. 31, 1992 for "Determining Bound and Unbound Fluid Volumes Using Nuclear Magnetic Resonance Pulse Sequences", now U.S. Pat. No. 5,363,041.

FIELD OF THE INVENTION

The invention concerns nuclear magnetic resonance (NMR) pulse sequences which are used in evaluating earth formations. More specifically, the invention relates to NMR pulse sequences which are used by a well logging tool and are interpreted to measure earth formation properties.

BACKGROUND OF THE INVENTION

Cross-reference is made to co-pending U.S. patent application Ser. No. 07/800,339 to A. Sezginer et al. for "Nuclear Magnetic Resonance Pulse Sequences for Detecting Bound Fluid Volume," filed Nov. 27, 1991.

Nuclear magnetic logging tools, such as disclosed in U.S. Pat. Nos. 4,933,638 to Kenyon et al. for "Borehole Measurement of NMR Characteristics of Earth Formations, and Interpretations Thereof"; and 5,055,787 and 5,055,788 both to Kleinberg et al. for "Borehole Measurement of NMR Characteristics of Earth Formations", measure the number and nuclear magnetic resonance (NMR) relaxation rates of hydrogen atoms in the pore space of rocks by measuring the amplitude and decay rate of signals resulting from pulse-echo sequences. In essence, the nuclear magnetic logging tools send a stream of RF-pulses into the formation and monitor the returning pulses which are called spin echoes. The measurements made are typically cyclical, with each cycle taking up to several seconds. Interpretation algorithms are then used to find the formation properties of interest.

The signal measured by a nuclear magnetic logging tool, such as CMR, mark of Schlumberger (Combined Magnetic Resonance) tool, formerly the PNMT, mark of Schlumberger (Pulsed Nuclear Magnetism Tool) is proportional to the mean density of hydrogen nuclei in the fluid that occupies the pore-space. Since the hydrogen density in water and liquid hydrocarbons are approximately constant, the detected signal can be calibrated to give the volume fraction of the fluid occupying the pore space.

NMR relaxation of a water saturated porous rock is not a simple exponential relaxation. Pores of rocks are in a fast diffusion regime (Latour, L. L., R. L. Kleinberg and A. Sezginer, Journal of Coll. and Interf. Science, Vol. 150, No. 2, May 1992) where the NMR signal from each pore is approximately single-exponential, and the relaxation time is proportional to the volume to surface ratio of the pore. Several researchers have demonstrated for water saturated sandstones and for synthetic porous specimens that the pore size distribution is closely related to the distribution of NMR relaxation times. Furthermore, it has been shown that the distributions of spin-lattice relaxation time $T_1$ and spin-spin relaxation time $T_2$ are very similar, and the ratio $T_1/T_2$ is in the relatively narrow range of 1.0 to 2.6 for sedimentary rocks. See Kleinberg et al., "T1/T2 Ratio and Frequency Dependence in Porous Sedimentary Rocks", Jnl of Colloid and Interface Science 158, 195–198 (1993). Therefore, distributions of both spin-lattice and spin-spin relaxation times carry the same information, namely the distribution of volume to surface ratios of pores. For example, an inversion-recovery measurement (Farrar, T. C. and E. D. Becker, *Pulse and Fourier Transform NMR*, Academic Press, 1971) which reveals spin-lattice relaxation, will produce a signal, m(t), that is a superposition of relaxations at different rates:

$$m(t) = \int_0^\infty a(T_1)(1 - 2e^{-t/T_1}) dT_1$$

where $a(T_1)dT_1$ is the volume fraction of the fluid whose spin-lattice relaxation time is between $T_1$ and $T_1+dT_1$.

Water that is bound to clay minerals, water in pores that are too small to be flushed by a feasible pressure gradient, and heavy (viscous) hydrocarbons all relax rapidly. Fluids that relax slowly have low viscosity and reside in large pores. Hence, the slowly relaxing fluids can be produced, that is, pumped to the surface, provided there is sufficient permeability. It has been shown that bound and unbound (producible) fluids can be distinguished by their relaxation times in water saturated rock samples. See C. Straley, C. E. Morriss, W. E. Kenyon, and J. J. Howard, "NMR in Partially Saturated Rocks: Laboratory Insights on Free Fluid Index and Comparison with Borehole Logs," presented at the annual SPWLA meeting, Midland, Tex., 1991. The volume fraction of unbound and bound fluids (UFV and BFV) and porosity $\Phi$ are related to the relaxation-time distribution function a(T1) as follows:

$$BFV = \int_0^{T_c} a(T_1) dT_1 \tag{c1}$$

$$UFV = \int_{T_c}^\infty a(T_1) dT_1 \tag{c2}$$

$$BFV + UFV = \Phi \tag{c3}$$

The cutoff relaxation time $T_c$ distinguishing bound fluids from unbound fluids is empirically determined to be 50 msec for spin-lattice relaxation and 33 msec for spin-spin relaxation for water saturated sandstones and for 100 psi capillary pressure. The cutoff poresize, hence the cutoff relaxation-time $T_c$, that divides the bound and unbound fluids depend on the differential pressure applied to produce the fluid.

BFV and UFV add up to porosity $\Phi$ which is the total volume fraction of fluids in the rock that are observable by the NMR logging instrument. Hydrogen nuclei in the rock matrix and some of the clay-bound water relax too rapidly and are not detected by the CMR. Therefore, hydration water and a fraction of clay-bound water is not included either in the BFV or porosity measured by the CMR.

UFV is conceptually the same as the free fluid index (FFI) and BFV is conceptually similar to but not necessarily equal to the volume fraction of irreducible water, $\Phi S_{irr}$. Bound fluid volume and irreducible water can differ when BFV includes heavy oil or when it misses part of the clay-bound water because of limitations of the logging instrument.

The BVF, the volume fraction of rapidly relaxing fluid, can be measured faster than either the entire distibution function or porosity can be measured. Therefore, a rapid measurement that is tailored to give only BFV is less sensitive to motion of the logging tool. BFV can be logged at speeds that are standard in the industry (1800–3600 ft/hr). UFV can then be estimated by subtracting BFV from the porosity if porosity is known either from other logs or another logging pass of the CMR.

OBJECTS AND SUMMARY OF THE INVENTION

It is an object of the invention to provide an NMR pulse sequence logging tool, which, when used alone in a continuous logging mode, directly indicates bound fluid volume of an earth formation.

The invention concerns an apparatus and method for measuring an indication of an attribute of a volume of earth formation with a borehole tool for placement in a borehole in the earth formation. The invention involves: a) producing a static magnetic field from the borehole tool into the formation; b) producing oscillating magnetic fields from the borehole tool according to a selected pulse sequence in order to excite nuclei of fluids in the formation, the nuclei having substantially distinguishable relaxation rates; c) measuring with the borehole tool the induced signals which result from nuclei of fluid at one relaxing rate which is substantially distinguishable from that of other nuclei of the fluid in the formation; and d) determining from the measured signals corresponding to the nuclei of the one an indication of a producible fluid volume of the volume of earth formation.

BRIEF DESCRIPTION OF THE DRAWINGS

FIG. 3 Applying the weights shown in FIG. 2 to the spin echoes is equivalent to applying a filter function (solid curve) to the relaxation-time distribution. The actual filter function (solid curve) is an approximation to the ideal BFV filter function (dashed line).

DESCRIPTION OF THE PREFERRED EMBODIMENT

Figure 1:
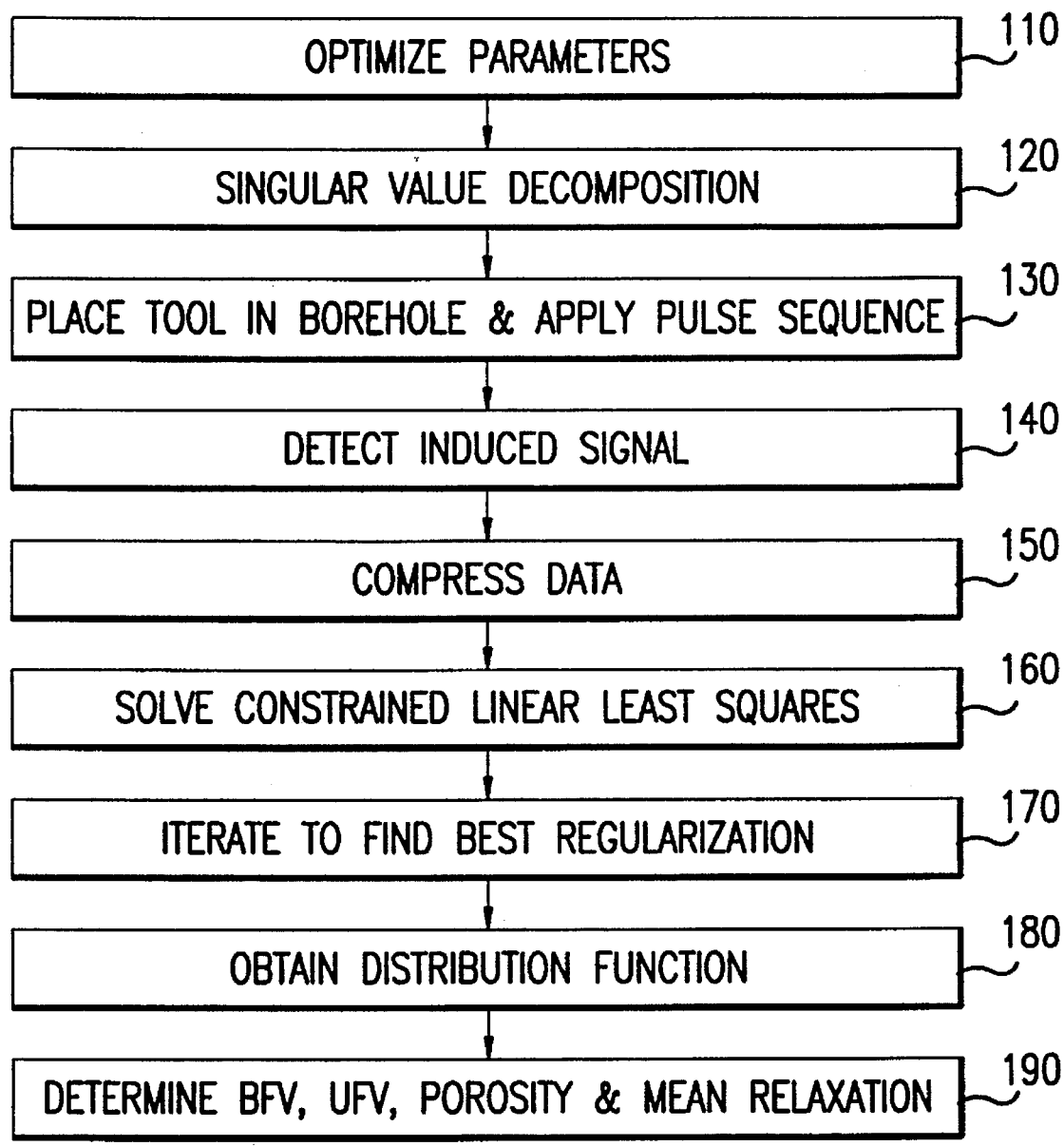
FIG. 1 is a flow chart illustrating steps for determining Bound Fluid volume (BFV) and as also described in U.S. patent application Ser. No. 07/800,339.

U.S. Pat. No. 5,363,041 describes techniques for determining Bound Fluid Volume. This application describes a generalized approach to the techniques of that patent.

The invention concerns the determination of bound and unbound (producible) fluid volumes in a formation. More specifically, the invention concerns a pulse-echo sequence by which the Bound Fluid Volume can be determined while the tool is being logged at a standard logging speed (1800–3600 ft/hr).

According to the invention, the static magnet of the CMR generates a field which aligns all nuclei of a fluid in a formation under evaluation into one magnetization direction (along the z-axis, for example). The nuclei are in a low energy state and will remain aligned until disturbed. The RF antenna of the CMR then generates a field according to a chosen CPMG pulse sequence. The first pulse of this sequence tips all such nuclei 90 degrees about the x-axis to the y-axis. The next pulse (and subsequent pulses) of the CPMG sequence then flips the nuclei 180 degrees about the y-axis to phase the nuclei. Thereafter, the nuclei generate a detectable magnetic field. The RF antenna of the CMR then detects resulting echo signals.

In the preferred embodiment for measuring BFV only, the measurement parameters of the CPMG pulse sequence are chosen so that the slowly relaxing spins do not substantially contribute to the received signal, thus the signal gives a direct approximation of BFV. The CPMG pulse sequence is chosen to effectively filter the detection of echo signals to those of nuclei of interest, giving a direct approximation of BFV. The preferred parameters defining the chosen pulse sequence are described above concerning FIG. 3.

By keeping the recovery time between the CPMG sequences short, only nuclei having short relaxation times (less than Tc, for example) have sufficient time to "relax" to the lowest energy state where they are aligned with the applied static field. It is only the echo signals resulting from these nuclei of rapidly relaxing, bound fluids which are detected in the formation under investigation. Because the timing of the NMR pulse sequence is short, nuclei having long relaxation times (greater than Tc, for example) barely recover before they are excited by the next CPMG pulse sequence. The slowly and rapidly relaxing nuclei are distinguished by the spin-lattice (T1) relaxation process. In this way, the nuclei having long relaxation times substantially maintain their zero net magnetization states and contribute negligibly to the detected signal. Thus, the fields excite nuclei substantially of the bound and unbound fluids which relax at rates (rapidly and slowly, respectively) which are substantially distinguishable from one another. The short recovery time of the CPMG sequence allows the tool to measure the induced signals which result from relaxing nuclei of one relaxing rate. Preferably, such nuclei are of bound fluid. Since the signal of the rapidly relaxing fluid can be measured rapidly, the BFV measurement can be logged at a rate approaching standard logging speeds. Porosity and then UFV can be determined either from other tools or a separate log by the CMR.

Measuring formation properties, such as spin-lattice relaxation time (T1); spin-spin relaxation time (T2) and porosity ($\Phi$) using NMR logging tools are described in U.S. Pat. No. 5,023,551 to Kleinberg et al. for "Nuclear Magnetic Resonance Pulse Sequences for Use with Borehole Logging Tools". The specification of U.S. Pat. No. 5,023,551 is incorporated by reference and is assigned to the same assignee as this invention.

FIG. 1 is a flow chart illustrating steps for determining Bound Fluid Volume (BFV) of a formation. Corresponding figures illustrating steps for determining BFV are described in U.S. Pat. No. 5,363,041 to Sezginer, which is incorporated by reference. At 210, a calibration is performed to determine the tool constants, in particular the factor that converts signal amplitude to volume fraction. At 220, desired parameters are entered, and an optimization is performed to find the optimal parameters. Specifically, the accuracy of the BFV estimate is optimized. See the discussion below concerning Equation (c10). At 230, the optimal parameters are used in pulse sequence programs. Steps 210 and 230 are described in U.S. Pat. No. 5,023,551 to Kleinberg et al. At 240, a CMR or PNMT logging tool, for example, is placed in the borehole. The CMR produces a static magnetic field in the volume of formation and then produces oscillating magnetic fields according to a phase-alternated Carr-Purcell-Meiboom-Gill (CPMG) sequence to induce signals in the volume which are measurable by the CMR in the borehole:

$$T_r \text{CPMG}^{(+)} T_r \text{CPMG}^{(-)} T_r \text{CPMG}^{(+)} T_r \text{CPMG}^{(-)} \quad (c4)$$

The CPMG sequences are separated by a fixed, relatively short recovery time ($T_r=20$ ms). Each CPMG sequence yields a short train of spin-echoes:

$$CPMG^{(\pm)} = 90°_{\pm x}[t_{cp}180°_y t_{cp} \pm echoj]3_{repeat\ for\ j=1,2,\ldots,J} \quad (c5)$$

where the part in brackets is repeated for $j=1, 2, \ldots, J$, and J is the number of echoes collected in a single CPMG sequence, and $t_{cp}$ is half of the echo spacing (about 0.2 ms). $90°_{\pm x}$ denotes an RF-pulse that causes the spins to rotate by a $90°$ angle about the axis $\pm x$. Similarly $180_y$ denotes an RF-pulse that causes a rotation by $180°$ about the axis y. The z-axis is parallel to the static field, the x-axis is in the direction of the circularly polarized component of the RF-field ($B_1$) that rotates in the same direction as the spins precess. The reference frame (x,y,z) rotates around the z axis with the angular frequency of the RF-field.

The echoes in pairs of phase alternated CPMG sequences are combined by subtracting the echoes in $CPMG^{(-)}$ from the echoes in the neighboring $CPMG^{(+)}$. This operation cancels a spurious baseline that may be present in the measurements. The resulting data vector [echo1, echo2, ..., echo J] can be stacked to improve the signal to noise ratio and then input to the processing algorithm.

The method presented here is also applicable if the CPMG sequence is replaced by the Cart-Purcell sequence with inversion (CPI) (Farrar, T. C. and E. D. Becker, *Pulse and Fourier Transform NMR*, Academic Press, 1971):

$$CPI^{(\pm)} = 90°_{\pm x}[t_{cp}180°_x t_{cp} \pm echoj\ t_{cp}\ 180°_{-x} t_{cp} +echoj+1] \quad (c5')$$

where the part in the brackets is repeated until J echoes are collected.

For purposes of this document, a "Cart-Purcell sequence" includes the CPMG and the CPI sequences described above, for example.

The parameters of the pulse sequence is obtained by the optimization procedure of step 220. At 250, the CMR tool then detects resulting signals which have been induced in the formation around the borehole. At 260, echo values are weighted and summed as discussed below concerning equation (c1) and FIG. 2, for example. At 270, total porosity is obtained. Total porosity can be obtained with the CMR itself. However, logging for porosity with this tool limits the logging speed. In a technique that allows higher logging speeds, total porosity is obtained using a Litho Density Tool (LDT, mark of Schlumberger), Compensated Neutron Log (CNL, mark of Schlumberger) or Sonic tool. Examples of tools for obtaining porosity are described in U.S. Pat. Nos. 3,453,433 to Alger et al. and 4,686,364 to Herron; 3,567,936 to Tittman and 3,567,935 to Nagel; and 3,590,228 to Burke and 3,896,668 to Anderson et al. U.S. Pat. Nos. 3,638,484 to Tixier and 4,310,887 to Suau describe deriving porosity data using density, neutron and sonic tools. At 280, the difference between the total porosity $\Phi$ obtained in step 270 and the bound fluid volume (BFV) obtained at step 260 yields unbound fluid volume UFV at 290. UFV indicates the amount of producible fluid that is contained in the formation around the borehole being logged.

An estimate of the BFV is obtained by a weighted sum of the echoes:

$$\overline{BFV} = \sum_{j=1}^{J} w_j echo_j \quad (c6)$$

The overbar denotes the estimate of the BFV as opposed to the quantity defined in (c1).

Figure 2C:
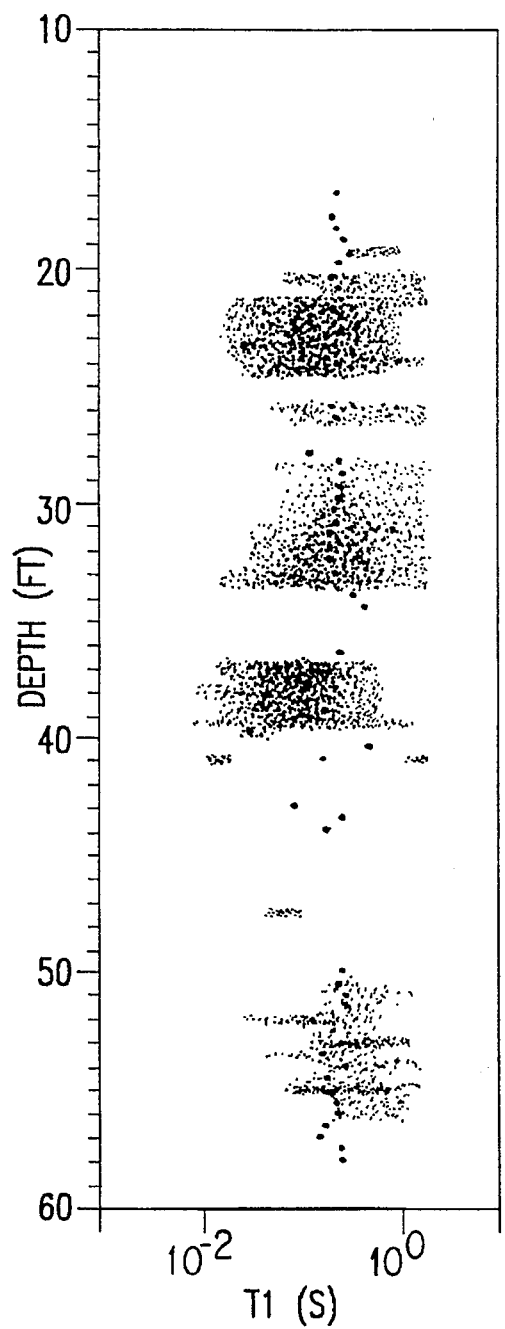
FIG. 2 is a chart illustrating an example of weights applied to spin echoes to obtain BFV as described in relation to FIG. 1.
Figure 2D:
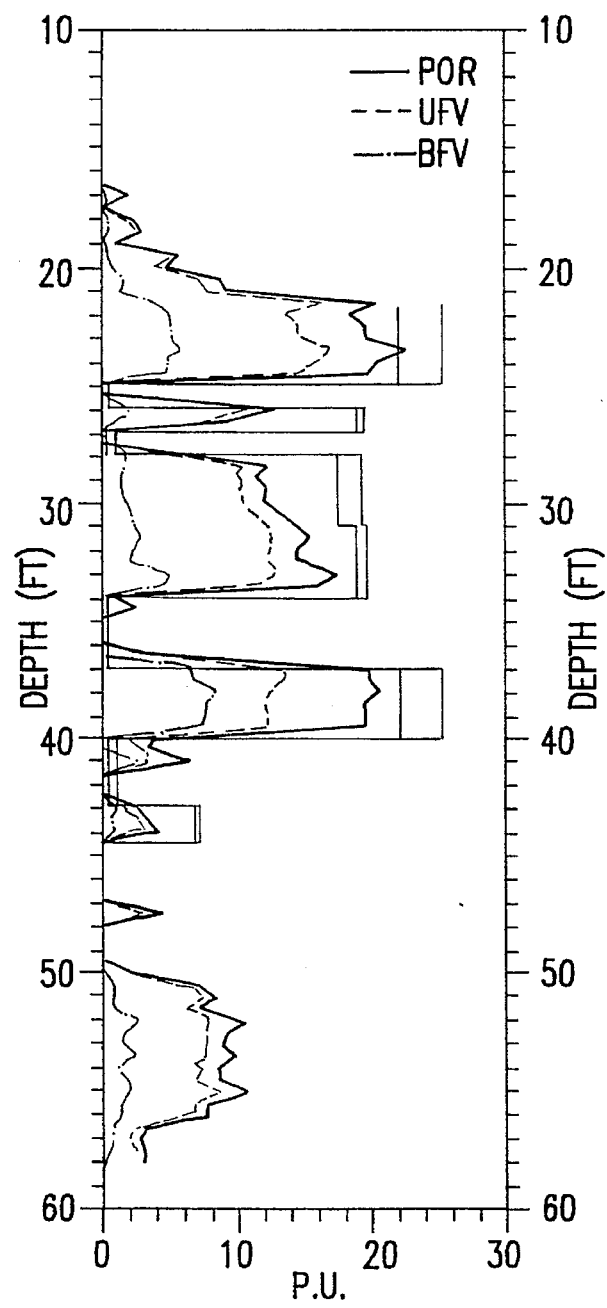

FIG. 2 is a chart illustrating an example of values of weights $w_j$ applied to echoes to obtain BFV. Echo-Weight is plotted as a function of Echo-Index. These values of the Echo-Weights in FIG. 2 were calculated for a Carr-Purcell spacing $t_{cp}=0.2$ ms and $T_1/T_2=1.5$. The ratio of spin-lattice relaxation time ($T_1$) to spin-spin relaxation time is assumed to be constant. The variance of the estimate after stacking for T seconds is $$Var[\overline{BFV}] = \frac{T_r + 2Jt_{cp}}{T} \sigma^2 w^2 \quad (c7)$$

$$w^2 = w_1^2 + w_2^2 + \ldots + w_J^2$$

where each echo has independently and identically distributed, zero-mean, additive Gaussian noise of standard deviation $\sigma$. $T_r$ is the length of the recovery-time in between the CPMG sequences. w is the norm of the vector $w=(w_1, w_2, \ldots, w_J)$. The estimator of BFV is a linear functional that acts on the relaxation-time distribution:

$$\overline{BFV} = \int_0^\infty f(T_1)a(T_1)dT_1 \quad (c8)$$

where $f(T_1)$ is the filter function resulting from the form (c6) of the estimator:

$$f(T_1) = [1 - e^{-T_r/T_1}] \sum_{j=1}^{J} w_j \exp\left(\frac{-2jt_{cp}(T_1/T_2)}{T_1}\right) \quad (c9)$$

Also taken into account in the computation, but not shown in (c9), is the fact that in a CPMG pulse-echo sequence the first spin-echo is about 61% of what would be expected from the extrapolation of the other echoes. This is a consequence of spin-dynamics in inhomogeneous fields and it has been verified by numerical solutions of Bloch's equation. The factor 61% was experimentally determined.

Figure 4:
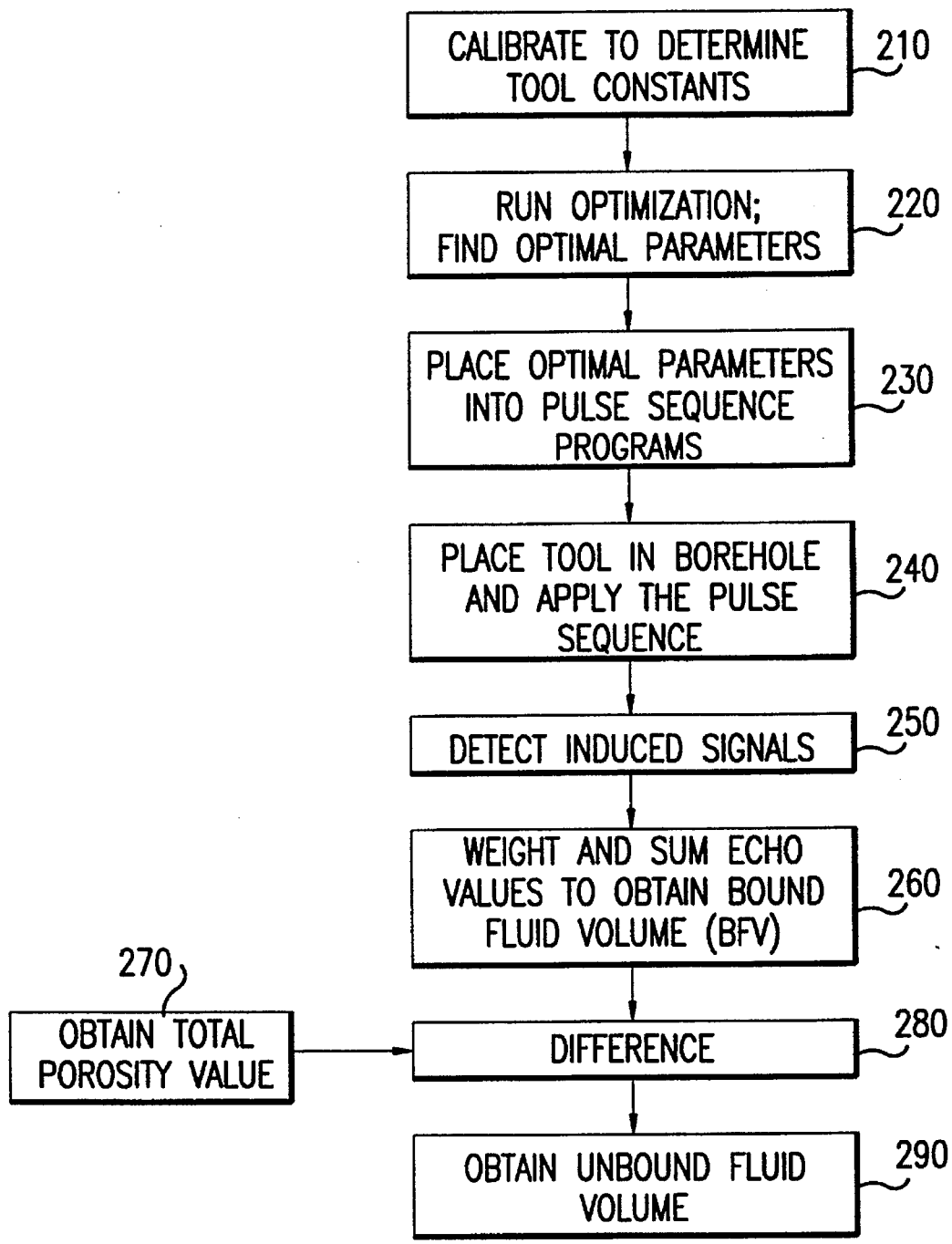
FIG. 4 illustrates one technique to find BFV by integrating the estimate of the relaxation-time distribution function to Tc. This is equivalent to applying the ideal filter function (dashed line in FIG. 3) to the esimated distribution function.
Figure 5:
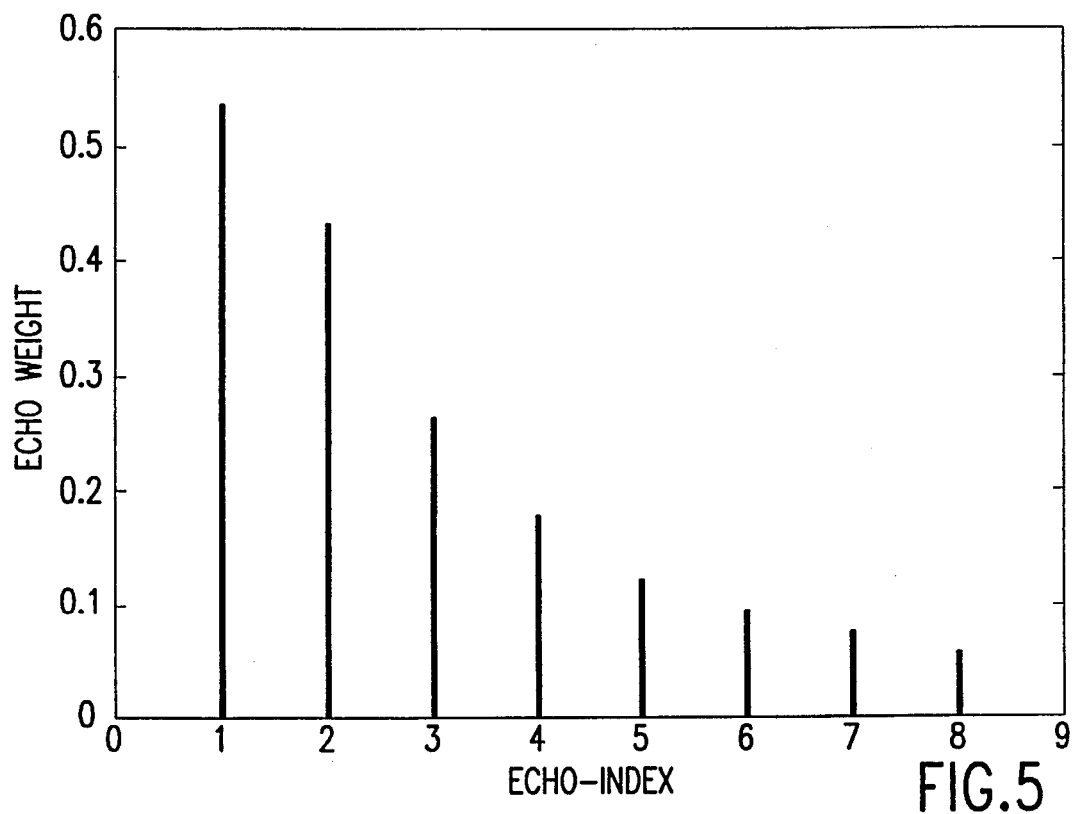
FIG. 5 illustrates another technique to find BFV by choosing a pulse sequence. This is equivalent to applying the filter function (solid line in FIG. 3) to the actual relaxation-time distribution function.
Figure 6:
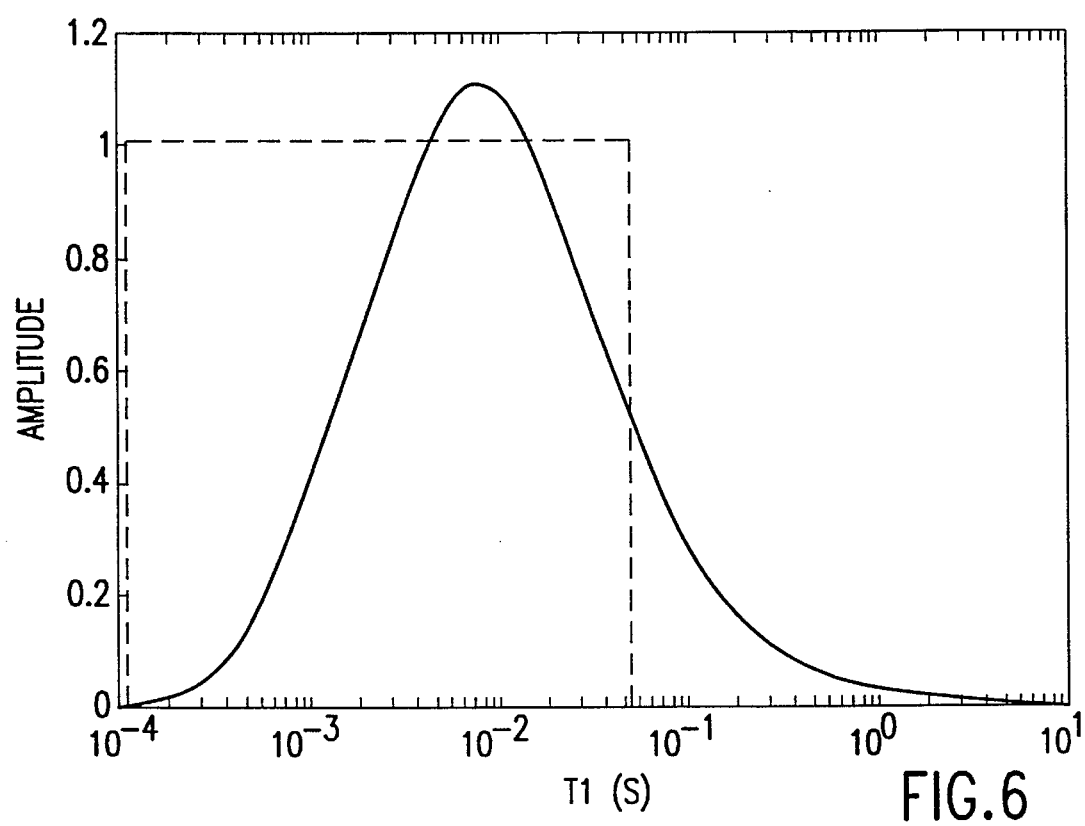

The action of the filter function f(T1) in Equations (c8) and (c9) is illustrated in FIG. 5. The estimate of BFV is equal to the area under the product of the relaxation-time distribution function (Curve A of FIG. 5) and the filter function f(T1) (Curve B of FIG. 5). This estimate of the BFV is an approximation to area labeled "BFV", under the relaxation-time distribution function (Curve A of FIG. 4). The estimate and the actual value of BFV would be the same if the filter function f(T1) were the ideal step function (the dashed curve in FIG. 3). However, the filter function f(T1) can only be an approximation (the solid curve in FIG. 3) to the ideal step function.

Curve A*B is the product of curve A and curve B. $\overline{BFV}$ is represented by the area under or the integration of curve A*B. $\overline{BFV}$ is the weighted sum of the echoes and is an acceptable direct approximation of BFV.

RELATION TO ANOTHER METHOD OF LOGGING UNBOUND FLUID VOLUME

In the approach illustrated in FIG. 4 and described in U.S. patent application Ser. No. 07/800,339, the spins are polarized until they substantially reach their equilibrium state before each CPMG sequence, and echo signals are detected until transverse relaxation of nuclei is substantially complete. The specification of U.S. patent (Ser. No. 800,339) is incorporated by reference. Then the entire relaxation-time distribution (Curve A of FIG. 4) is estimated. This distribution curve is integrated over a period extending from zero relaxation-time to an empirically determined cutoff relaxation-time Tc to find BFV (the area labelled "BFV" under Curve A of FIG. 4). The entire distribution curve A is integrated to find Porosity. The entire area under curve A from time zero to maximum relaxation time of nuclei in the formation (approximately 2–3 seconds) represents Porosity. UFV, the volume of producible fluid in the formation, is then found by subtracting BFV from Porosity. The area labelled "UFV" under curve A after Tc represents Unbound Fluid Volume. Thus, BFV, UFV, and Porosity are determined using only the CMR. In the approach illustrated in FIG. 4, the recovery time before each CPMG sequence has to be on the order of T1 or larger, and the length of each CPMG sequence has to be on the order of T2 or larger. The measurement cycle can take as much as 2 seconds. Although the resulting estimate of BFV and UFV are accurate, the measurement illustrated in FIG. 4 has to be logged at a relatively low speed. By contrast, in the preferred embodiment of measuring BFV only, illustrated in FIGS. 1, 2, 3, 5, BFV can be logged faster because its measurement cycle is on the order of 25 msec.

OPTIMIZATION OF THE MEASUREMENT PARAMETERS

The adjustable parameters of the measurement, namely, $(w_1, w_2, \ldots, w_J)$, $T_r$, J are determined by two competing requirements. First, according to (c1) and (c8), $$f(T_1) \approx \begin{cases} 1, \text{ if } T_1 < T_c \\ 0, \text{ if } T_1 > T_c \end{cases} \quad (c10)$$

must be satisfied. On the other hand, according to (c7), w must be kept small in order to keep the statistical error small. Equation (c10) has been solved for the weights in the least square sense subject to the constraint w<constant. The parameters $T_r$ and J have been determined by trial and error to minimize the fit error in (c10). The result of the optimization yielded J=8, $T_r$=20 ms and a set of weights wj that decrease with increasing j which are shown in FIG. 2.

FIG. 3 is a chart illustrating an example of actual and ideal filter functions. Amplitude is plotted as a function of spin lattice relaxation time $T_1$ in seconds. The solid line shows an actual filter function $f(T_1)$ and the dashed line shows an ideal filter function. In this case, where $t_{cp}$=0.2 ms and $T_1/T_2$=1.5, the optimal parameters are: recovery time $T_r$=20 ms, J=8, and the weights are as shown in FIG. 2. For $t_{cp}$=0.2 ms, $T_r$=20 ms, J=8, σ=10 porosity units, and signal accumulation time T=1 s, the standard deviation of BFV is 1.2 porosity units.

As intended, the filter function (solid curve in FIG. 3) has a long-time cutoff around 50 msec because slowly relaxing components can not recover in the short (20 msec) recovery time. There is also a short-time cutoff around 2 msec because the components that significantly decay before the first echo cannot be observed.

It has been shown that the distributions of T1 and T2 are similar. Therefore, the distribution of either $T_2$ or $T_1$ may be considered to evaluate BFV and UFV. It has been shown that the ratio of T1/T2, depending on the rock formation under evaluation, is in the range 1.0–2.6 for sandstones and carbonates by Kleinberg et al. See "T1/T2 Ratio and Frequency Dependence in Porous Sedimentary Rocks", Jnl of Colloid and Interface Science 158, 195–198 (1993). When using spin-lattice relaxation time T1, Tc is 50 msec, for example. When using spin-spin relaxation time T2, Tc is 30 msec, for example.

Thus, according to this invention, through the use of the shortened pulse sequence, a sum of the resulting echo signals detected by the CMR is a direct approximation of BFV. The PNMT can log the formation at a rate approaching standard logging speeds. Porosity and then UFV can be determined from other tools. Thus, generally excited nuclei relaxing at a chosen rate (rapidly or slowly) will induce signals from the fluid of the formation. These signals indicate the producible fluid in the formation.

I claim:
1. A method for indicating an attribute of an earth formation with a borehole tool having a magnetic device for producing static magnetic fields in a volume of a formation, a an antenna for producing oscillating magnetic fields in a volume of a formation and for detecting echo signals, the method comprising:
  a) producing a static magnetic field in a volume of formation;
  b) producing oscillating magnetic fields according to a selected pulse sequence in order to excite nuclei of fluids in the volume wherein some nuclei relax slowly and some nuclei relax rapidly relative to each other;
     i) producing at least one pulse of the pulse sequence such that the rapidly relaxing nuclei produce an echo signal in the volume of formation; and
     ii) producing a subsequent pulse of the pulse sequence substantially after the rapidly relaxing nuclei produce an echo signal in the volume of formation and before the slowly relaxing nuclei produce an echo signal in the formation;
  c) receiving the echo signals from the formation due to the rapidly relaxing nuclei, the slowly relaxing nuclei substantially not contributing to the received signals; and
  d) determining from the measured signals corresponding to the rapidly relaxing nuclei an indication of bound fluid volume (BFV) of the volume of earth formation.

2. An apparatus for indicating an attribute of an earth formation with a borehole tool having a magnetic device for producing static magnetic fields in a volume of a formation, an antenna for producing oscillating magnetic fields in a volume of a formation and for detecting echo signals;
  the antenna comprising a means for producing oscillating magnetic fields according to a Carr-Purcell-Meiboom-Gill (CPMG) sequence in order to excite nuclei of fluids in the volume wherein some nuclei relax slowly and some nuclei relax rapidly relative to each other, the means for producing oscillating magnetic fields also for:
     i) producing at least one pulse of the pulse sequence such that the rapidly relaxing nuclei produce an echo signal in the volume of formation; and
     ii) producing a subsequent pulse of the pulse sequence substantially after the rapidly relaxing nuclei produce an echo signal in the volume of formation and before the slowly relaxing nuclei produce an echo signal in the formation;
  the antenna also comprising a means for receiving the signals induced in the formation due to the rapidly relaxing nuclei, the slowly relaxing nuclei substantially not contributing to the received signals; and
  the apparatus further comprising a means for determining from the received signals corresponding to the rapidly relaxing nuclei an indication of bound fluid volume (BFV) of the volume of earth formation.

3. A method for indicating an attribute of an earth formation with a borehole tool for placement in a borehole, the steps comprising:
  a) producing a static magnetic field from the borehole tool into the formation;
  b) producing oscillating magnetic fields from the borehole tool according to a selected pulse sequence in order to induce signals from selected nuclei of the formation which are measurable by the borehole tool in the borehole;
  i) producing at least one pulse of the pulse sequence such that the rapidly relaxing nuclei relative to a selected relaxation time, produce an induced signal in the volume of formation; and
  ii) producing a subsequent pulse of the pulse sequence substantially after the rapidly relaxing nuclei produce an induced signal in the volume of formation and before the slowly relaxing nuclei, relative to the selected relaxation time, produce an induced signal in the formation;
c) measuring with the borehole tool the induced signals which substantially correspond to rapidly relaxing nuclei having relaxation times shorter than the selected relaxation time, the slowly relaxing nuclei producing negligible induced signals; and
d) determining from the measured signals of the nuclei having rapid relaxation times an indication of non-predicable fluid volume of the volume of earth formation.

4. A method according to claim 3, wherein the induced signals comprise at least spin-echoes, and the step of measuring the induced signals comprises performing a weighted integration of at least portions of the echoes.

5. The method of claim 4, wherein the selected relaxation time is a cutoff spin-spin relaxation time of approximately 33 milliseconds.

6. The method of claim 5, wherein the selected relaxation time is a cutoff spin-lattice relaxation time of approximately 50 milliseconds.

7. The method of claim 6, wherein the borehole tool is moved upward through the borehole at a speed and the weighting of the echo values is substantially independent of the speed of the borehole tool.

8. An apparatus for indicating an attribute of a formation for placement in a borehole, the apparatus comprising:
  a) a magnet for producing a static magnetic field into the formation;
  b) an antenna for producing oscillating magnetic fields according to a selected pulse sequence in order to induce signals from selected nuclei in the formation, wherein such signals are measurable in the borehole, the antenna
    i) producing at least one pulse of the pulse sequence such that the rapidly relaxing nuclei produce an induced signal in the volume of formation relative to a selected relaxation time; and
    ii) producing a subsequent pulse of the pulse sequence substantially after the rapidly relaxing nuclei produce an induced signal in the volume of formation and before the slowly relaxing nuclei produce an induced signal in the formation;
  c) a means for measuring the induced signals which correspond to the rapidly nuclei having relaxation times shorter than a selected time, the slowly relaxing nuclei producing negligible induced signals; and
  d) a means for determining from the measured signals an indication of non-predicable fluid volume of the volume of earth formation.

9. An apparatus according to claim 8, wherein the induced signals comprise at least spin-echoes, and the means for determining comprises a means for weighting and integrating at least portions of the echoes.

10. The apparatus of claim 9, wherein the selected time is a cutoff spin-spin relaxation time of approximately 33 milliseconds.

11. The apparatus of claim 9, wherein the selected time is a cutoff spin-lattice relaxation time of approximately 50 milliseconds.

12. The apparatus of claim 11, wherein the apparatus is a borehole tool which is moved upward through the borehole at a speed and the weighting of the echo values is substantially independent of the speed of the borehole tool.

13. A method for measuring an indication of an attribute of a volume of earth formation with a borehole tool for placement in a borehole in the earth formation, the steps comprising:
  a) producing a static magnetic field from the borehole tool into the formation;
  b) producing oscillating magnetic fields from the borehole tool according to a selected pulse sequence in order to excite nuclei of fluids in the formation;
    i) producing at least one pulse of the pulse sequence such that the nuclei relaxing at a first rate produce an induced signal in the volume of formation; and
    ii) producing another pulse of the pulse sequence such that nuclei relaxing at a second rate produce a negligible induced signal in the formation;
  c) measuring with the borehole tool the induced signals which result from nuclei relaxing at the first rate in the formation, nuclei relaxing at the second rate producing negligible induced signals; and
  d) determining from the measured signals corresponding to the nuclei relaxing at the selected rate an attribute of the volume of earth formation.

14. A method according to claim 13, wherein the induced signals comprise at least spin-echoes, and the step of measuring the induced signals comprises weighting and integrating at least portions of the echoes.

15. The method of claim 13, including determining predicable fluid volumes according to rates of relaxation of the nuclei.

16. An apparatus for indicating an attribute of a volume of earth formation for placement in a borehole, the apparatus comprising:
  a) a magnetic device for producing a static magnetic field in the formation;
  b) an antenna for producing oscillating magnetic fields according to a selected pulse sequence in order to excite nuclei of fluids in the formation, the antenna
    i) producing at least one pulse of the pulse sequence such that the nuclei relaxing at a first rate produce an induced signal in the volume of formation; and
    ii) producing another pulse of the pulse sequence such that nuclei relaxing at a second rate produce a negligible induced signal in the formation;
  c) a means for measuring with the borehole tool the induced signals which result from nuclei relaxing at the first rate in the formation, nuclei relaxing at the second rate producing negligible induced signals; and
  d) a means for determining from the measured signals an indication an attribute of earth formation.

17. An apparatus according to claim 16, wherein the induced signals comprise at least spin-echoes, and the means for determining comprises a means for weighting and integrating at least portions of the echoes.

18. The apparatus of claim 17, including a means for determining predicable fluid volumes according to rates of relaxation of the nuclei.

19. A method for indicating an attribute of an earth formation with a borehole tool, the steps comprising:
  a) producing a static magnetic field from the borehole tool into the formation;

b) producing oscillating magnetic fields from the borehole tool according to a selected pulse sequence in order to excite nuclei of fluids in the formation, the nuclei having substantially distinguishable relaxation rates, the pulse sequence being such that nuclei relaxing at a first rate produce a detectable induced signal in the formation and nuclei relaxing at a second rate produce a negligible induced signal;

c) measuring with the borehole tool the induced signals which result from nuclei relaxing at the first rate which is substantially distinguishable from that of nuclei relaxing at the second rate and measuring substantially no induced signals resulting from nuclei relaxing at the second rate: and d) determining from the measured signals corresponding to the nuclei relaxing at the first rate an indication of an attribute of the volume of earth formation.

20. An apparatus for indicating an attribute of an earth formation for placement in a borehole, the apparatus comprising:

a) a magnetic device for producing a static magnetic field into the formation;

b) an antenna for producing oscillating magnetic according to a selected pulse sequence in order to excite nuclei of fluids in the formation, the nuclei having substantially distinguishable relaxation rates, the pulse sequence being such that nuclei relaxing at a first rate produce a detectable induced signal in the formation and nuclei relaxing at a second rate produce a negligible induced signal;

c) a means for measuring the induced signals which result from nuclei relaxing at the first rate which is substantially distinguishable from that of nuclei relaxing at the second rate in the formation and for measuring substantially no induced signals resulting from nuclei relaxing at the second rate; and d) a means for determining from the measured signals corresponding to the nuclei relaxing at the first rate an indication of an attribute of the volume of earth formation.

* * * * *